(12) United States Patent
Shinada et al.

(10) Patent No.: US 8,797,041 B2
(45) Date of Patent: Aug. 5, 2014

(54) DISCHARGE IONIZATION CURRENT DETECTOR

(75) Inventors: Kei Shinada, Uji (JP); Shigeyoshi Horiike, Uji (JP); Takahiro Nishimoto, Soraku-gun (JP); Katsuhisa Kitano, Ibaraki (JP)

(73) Assignees: Shimadzu Corporation, Kyoto-shi (JP); Osaka University, Osaka (JP)

( * ) Notice: Subject to any disclaimer, the term of this patent is extended or adjusted under 35 U.S.C. 154(b) by 465 days.

(21) Appl. No.: 13/092,003

(22) Filed: Apr. 21, 2011

(65) Prior Publication Data
US 2011/0260732 A1   Oct. 27, 2011

(30) Foreign Application Priority Data

Apr. 26, 2010 (JP) ................. 2010-100647

(51) Int. Cl.
*G01N 27/62* (2006.01)
*G01N 27/70* (2006.01)
*G01N 27/68* (2006.01)

(52) U.S. Cl.
CPC ........... *G01N 27/70* (2013.01); *G01N 27/68* (2013.01); *G01N 27/62* (2013.01)
USPC ........................................ 324/464

(58) Field of Classification Search
CPC ......... G01R 27/70; G01R 27/68; G01R 27/62
USPC .......................................... 324/464
See application file for complete search history.

(56) References Cited

U.S. PATENT DOCUMENTS

| 5,394,092 A | 2/1995 | Wentworth et al. ........... 324/464 |
| 5,892,364 A | 4/1999 | Monagle ....................... 324/464 |
| 6,842,008 B2 | 1/2005 | Stearns et al. |
| 8,229,323 B2 * | 7/2012 | Teramura ..................... 399/151 |
| 8,421,470 B2 * | 4/2013 | Kitano et al. ................. 324/464 |

FOREIGN PATENT DOCUMENTS

| CN | 101027550 A | 8/2007 |
| WO | WO 2009/119050 A1 | 10/2009 |

OTHER PUBLICATIONS

Katsuhisa Kitano et al., "Generation of Atmospheric Pressure Cold Plasma Jets for Applications to Chemical Reaction and Sterilization", Extended Abstract of CAPSA2007, The 3rd International Congress on Cold Atmospheric Pressure Plasmas: Sources and Applications.

(Continued)

*Primary Examiner* — Amy He
(74) *Attorney, Agent, or Firm* — Bingham McCutchen LLP

(57) ABSTRACT

A discharge ionization current detector using a low-frequency dielectric barrier discharge with an improved S/N ratio is provided. A current detector 20 is disposed between an excitation high-voltage power source 8 and a discharge electrode 5 to detect a discharge current flowing in pulses due to plasma generation. The detection signal of the current detector 20 and an output signal from a current amplifier 18 for amplifying an ion current are inputted into an output extraction unit 21. The output extraction unit 21 detects a precipitous-rise portion of the discharge current detection signal and generates a trigger signal, and then extracts an ion current signal for a predetermined time period from the trigger signal. This can remove an influence of a noise appearing in a signal during a time period where no plasma emission is generated, thereby improving the S/N ratio of the detection signal.

6 Claims, 3 Drawing Sheets

(56) References Cited

OTHER PUBLICATIONS

Kei Shinada et al., "Excited Ionization Current Detector for Gas Chromatography by Atmospheric Pressure Microplasma", Extended Abstract of 55th Meeting of Japan Society of Applied Physics and Related Societies in 2008 Spring.

Kei Shinada et al., "Excited Ionization Current Detector for Gas Chromatography by Atmospheric Pressure Microplasma (II)", Extended Abstract of 69th Annual Meeting of Japan Society of Applied Physics in 2008 Autumn.

Chinese language office action dated Jan. 23, 2013 and its English language translation issued in corresponding Chinese application 201110105579.4.

* cited by examiner

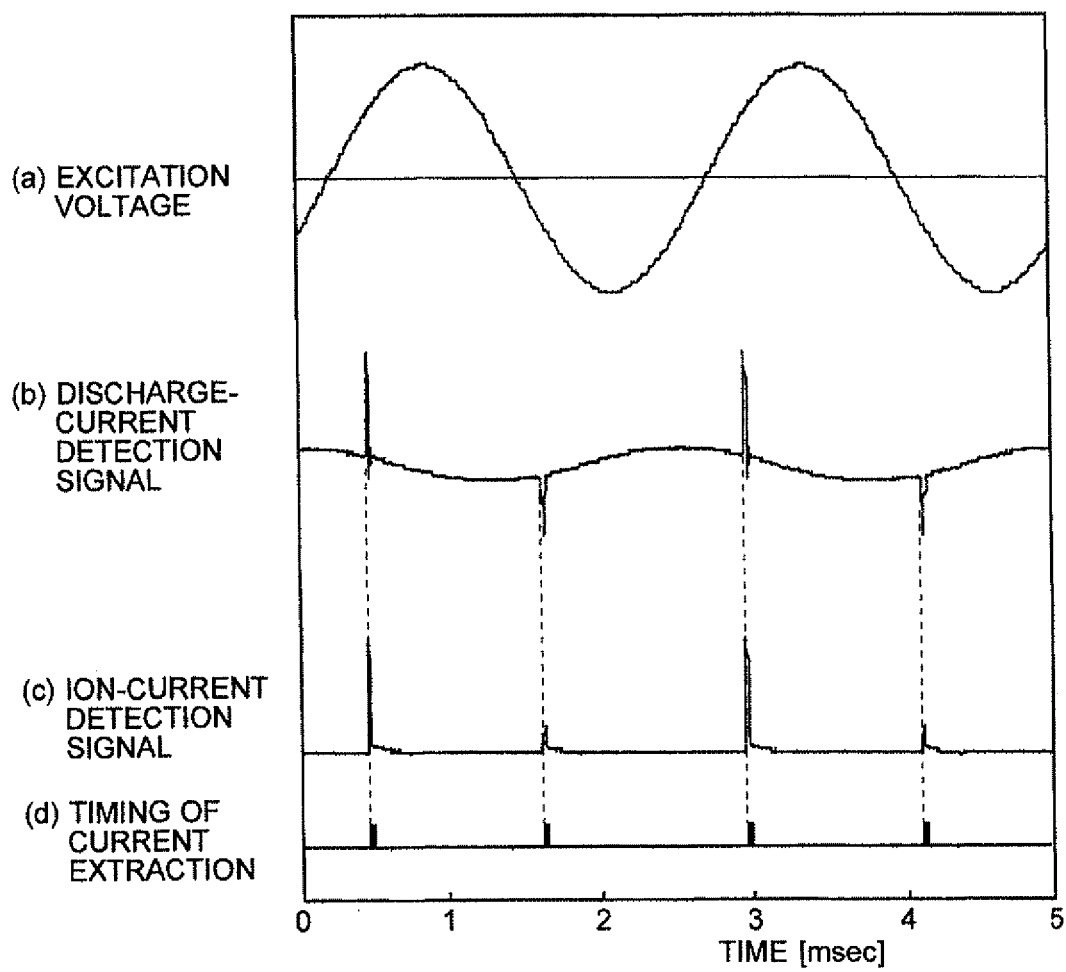
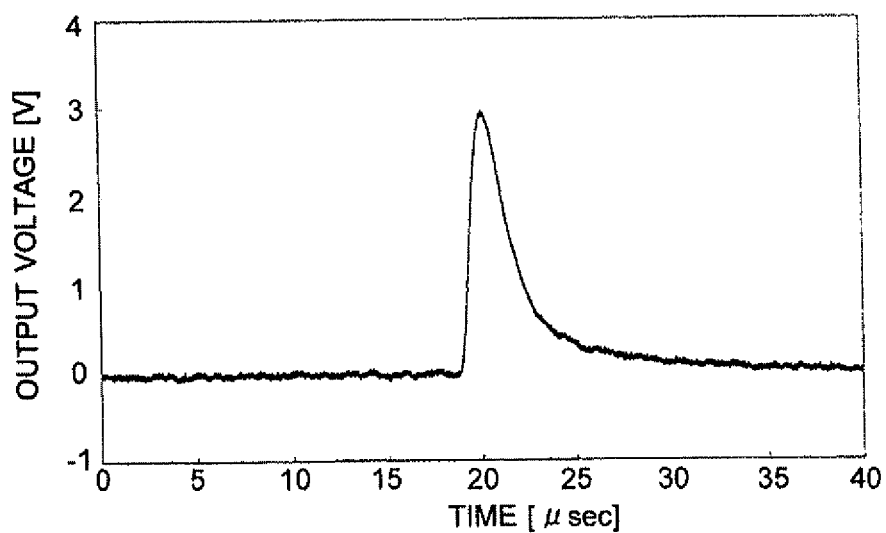

DISCHARGE IONIZATION CURRENT DETECTOR

The present invention relates to a discharge ionization current detector primarily suitable as a detector for a gas chromatograph (GC), and more specifically to a discharge ionization current detector using a low-frequency barrier discharge.

BACKGROUND OF THE INVENTION

As a detector for a gas chromatograph, various types of detectors have been practically applied, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not sufficiently low. (2) Its ionization efficiency for alcohols, aromatic substances, and chlorine substances is low. (3) It requires hydrogen, which is a highly hazardous substance; therefore, an explosion-proof apparatus or similar kind of special equipment must be provided, which makes the entire system more difficult to operate.

On the other hand, as a detector capable of high-sensitivity detection of various compounds from inorganic substances to low-boiling organic compounds, a pulsed discharge detector (PDD) has conventionally been known (for example, refer to U.S. Pat. No. 5,394,092). In the PDD, the molecules or atoms of helium or another substance are excited by a high-voltage pulsed discharge. When those molecules return from the excited state to the ground state, they emit the light with high optical energy. This optical energy is utilized to ionize a molecule or atom to be analyzed, and an ion current brought by the generated ions is detected to obtain a detection signal corresponding to the amount (concentration) of the molecule to be analyzed.

In most cases, the PDD can attain higher ionization efficiencies than the FID. For example, the ionization efficiency of the FID for propane is no higher than 0.0005%, whereas the PDD can achieve a level as high as 0.07%. Despite this advantage, the dynamic range of the PDD is not as wide as that of the FID; the fact is that the former is one or more digits lower than the latter. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, refer to U.S. Pat. No. 5,892,364). This detector uses a low-frequency Alternating-Current (AC)-excited dielectric barrier discharge (which is hereinafter referred to as the low-frequency barrier discharge) to create a stable and steady state of plasma. The plasma created by the low-frequency barrier discharge is non-equilibrium atmospheric pressure plasma, which gas temperature does not become hot as easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady state of plasma can be easily obtained. Based on these findings, the present inventors have conducted various kinds of research on the discharge ionization current detector using a low-frequency barrier discharge and have made many proposals on this technique (for example, refer to the following documents: International Publication No. WO2009/119050, Shinada et al., "Taikiatsu Maikuro-purazuma Wo Mochiita Gasu Kuromatografu You Ion-ka Denryuu Kenshutsuki (Excited Ionization Current Detector for Gas Chromatography by Atmospheric Pressure Microplasma)", *Extended Abstracts of 55$^{th}$ Meeting of Japan Society of Applied Physics and Related Societies* in 2008 Spring; and Shinada et al., "Taikiatsu Maikuro-purazuma Wo Mochiita Gasu Kuromatografu You Ion-ka Denryuu Kenshutsuki (II) (Excited Ionization Current Detector for Gas Chromatography by Atmospheric Pressure Microplasma: Part II)", *Extended Abstracts of 69$^{th}$ Meeting of Japan Society of Applied Physics* in 2008 Autumn).

As explained previously, the low-frequency barrier discharge creates a stable plasma state and is also advantageous for noise reduction. Therefore, the discharge ionization current detector using the low-frequency barrier discharge can attain a high S/N ratio. With respect to its ionization efficiency, although it can attain higher ionization efficiency than that of the FID, its ionization efficiency is equal to or lower than 0.1% at a maximum at present. Accordingly, an ionization current noise corresponding to a required detection limit (a level as high as 1 pgC/sec) is on the order equal to or lower than 1 pA. The implementation thereof requires a sufficient suppression of an influence of a disturbance noise (such as an electromagnetic noise suddenly appearing in a signal cable, or a noise caused by thereto-electromotive force due to a temperature difference) caused by a measurement system. However, it is practically impossible to completely prevent the invasion of a noise from certain parts of the device, such as an opening for introducing and/or discharging a sample gas or a carrier gas. Furthermore, the detection cell is heated up to approximately 400 degrees Centigrade for the detection of a high-boiling component. Therefore, it is very difficult to completely suppress the influence of the thermo-electromotive force occurring between the heated detector cell and a circuit at room temperature.

SUMMARY OF THE INVENTION

The present invention has been made to solve the previously described problems, and a purpose thereof is to provide a discharge ionization current detector capable of diminishing an influence of a disturbance noise caused by a sudden-appearance of an electromagnetic noise or thereto-electromotive force due to a temperature-difference as much as possible so as to obtain an ionization current signal originating from a component to be detected at high sensitivity and accuracy.

In a low-frequency dielectric barrier discharge, plasma is created by generating electric discharge in such a manner that a low-frequency Alternating Current (AC) voltage having a frequency range from 50 Hz to 100 kHz is applied to an electrode. However, the electric discharge itself does not occur continuously, but occurs intermittently. Accordingly, a plasma emission also occurs intermittently. On the other hand, the present inventors have found, from various experiments and studies, that a sample component is ionized primarily by photoionization with plasma light, and the lifetime of ions generated by the photoionization is comparatively short. This finding suggests that a time period for an ion current to flow into a detection electrode due to ions originating from a sample component to be detected is limited to a comparatively short time period from the plasma emission. Any signal obtained in a time period other than the previously described time period is primarily dominated by noises. The present invention has been made based on such perception and idea.

The present invention made to solve the previously described problems relates to a discharge ionization current detector including:

a discharge generation means for generating plasma from a predetermined gas by electric discharge, including a pair of electrodes with at least one surface covered with a dielectric material and a voltage application means for applying a low-frequency AC voltage to the electrodes; and a current detection means for detecting an ion current originating from a gas-phase sample component ionized by an action of the generated plasma, the discharge ionization current detector further comprising:

a) an emission timing detection means for detecting a timing of a plasma emission intermittently excited by the electric discharge from the discharge generation means; and b) a signal extraction means for acquiring a signal corresponding to the ion current detected by the current detection means at a timing synchronized with the plasma emission based on the detection result by the emission timing detection means.

Any type of gas selected from helium, argon, nitrogen, neon and xenon as well as any mixture thereof can be used as the predetermined gas.

The frequency of the low-frequency AC voltage applied to the electrode may be set in a range from 50 Hz to 100 kHz, and preferably in a range from 100 Hz to 20 kHz.

As one embodiment of the present invention, the emission timing detection means may serve as a current detection means for detecting a current supplied from the voltage application means to the electrodes. Although the low-frequency AC voltage is continuously applied to the electrodes from the voltage application means, the discharge current flows only when the electric discharge actually occurs to cause the plasma emission. Accordingly, the timing of the flow of the discharge current is synchronized with the plasma emission, so that the current detection means can indirectly detect the timing of the plasma emission.

The emission timing detection means may, of course, be constructed as a photodetection means for more directly detecting plasma emission light.

In a conventional discharge ionization current detector using a low-frequency dielectric barrier discharge, the ion current detected by a detection electrode is integrated, without particularly limiting the integration period, to be converted into a voltage signal. In this case, the integrated current includes an unnecessary electric current which is detected in a period of time where the plasma emission does not substantively occur (at least an emission having the intensity necessary for contributing to photoionization does not occur) and hence little current due to the ions originating from a sample component flows.

In contrast, according to the discharge ionization current detector of the present invention, the emission timing detection means directly or indirectly detects the timing of generation of a substantive plasma emission. The signal extraction means extracts a signal corresponding to the detected ion current at a timing synchronized with the plasma emission only for a specific time period, for example, in which the substantive plasma emission occurs, or for a time period from the substantive generation of the plasma emission to a time point which is set after the lapse of a predetermined time period from the termination of the plasma emission, taking a lifetime of ions into account. Specifically, for example, only the ion current detected during the aforementioned time period is integrated to obtain the voltage signal. Accordingly, the current primarily originating from a noise and being detected during a time period in which the current of the ions originating from a sample component to be detected should not be detected is not reflected in a voltage signal to be outputted.

According to the discharge ionization current detector of the present invention, a disturbance noise contained in a signal extracted as a detection output can be reduced, thereby improving the S/N ratio of the signal. As a result, the detection sensitivity or detection accuracy of the sample component can be enhanced.

According to a report from K. Kitano, "Nonequilibrium atmospheric pressure plasma jets with a single electrode and their applications to chemical reactions and sterilization", *Extended Abstract of CAPSA2007 (The 3$^{rd}$ International Congress on Cold Atmospheric Pressure Plasmas Sources and Applications)*, the state of the low-frequency dielectric barrier discharge is different between the case where the electric discharge occurs with an application of the positive voltage to the high-voltage electrode (positive-voltage discharge) and the case where the electric discharge occurs with an application of the negative voltage to the high-voltage electrode (negative-voltage discharge). The present inventors have also confirmed in an experiment that the plasma emission caused by the positive-voltage discharge has higher brightness than that caused by the negative-voltage discharge, and produces a larger ion-current flow than in the former case.

Accordingly, in the discharge ionization current detector according to the present invention, the signal extraction means preferably acquires a signal corresponding to an ion current detected by the current detection means at a timing synchronized with the plasma emission during a time period in which a positive voltage is applied to the high-voltage electrode between the pair of electrodes included in the discharge generation means based on the detection result by the emission timing detection means. This configuration enables the extraction of the detection signal having a further higher S/N ratio.

BRIEF DESCRIPTION OF THE DRAWINGS

FIG. 2 is a waveform diagram for illustrating operations of the discharge ionization current detector according to the present embodiment.

FIG. 3 is an enlarged diagram showing a peak of the ion-current detection signal shown in FIG. 2(*c*).

DETAILED DESCRIPTION OF A PREFERRED EMBODIMENT

Figure 1:
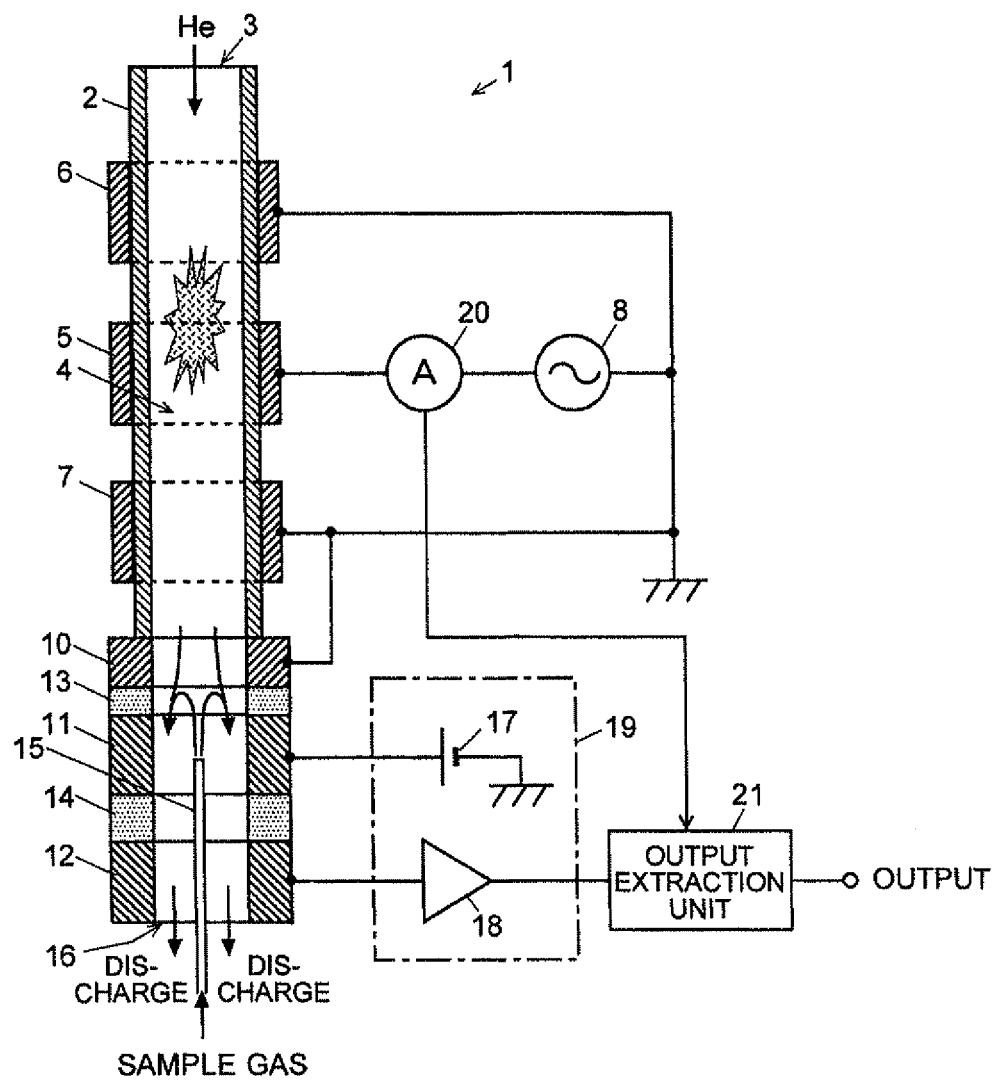
FIG. 1 is a schematic configuration diagram showing a discharge ionization current detector according to one embodiment of the present invention.

A discharge ionization current detector according to an embodiment of the present invention is hereinafter described with reference to the attached drawings. FIG. 1 is a schematic configuration diagram of the discharge ionization current detector according to the present embodiment.

A discharge ionization current detector 1 of the present embodiment includes a cylindrical tube 2 made of a dielectric material, such as quartz. The inner space of this tube 2 is a gas passage 4. For example, the cylindrical tube 2 may be a quartz tube having an outer diameter of 3.9 mm. Ring-shaped plasma generation electrodes 5, 6, and 7, which are made of a metal (e.g. stainless steel or copper), are circumferentially provided at predetermined intervals on the outer wall surface of the cylindrical tube 2. According to this design, the dielectric wall of the cylindrical tube 2 between the gas passage 4 and the plasma generation electrodes 5, 6 and 7 functions as a dielectric coating layer that covers the electrodes 5, 6 and 7, thereby enabling dielectric barrier discharge to occur.

Among the three plasma generation electrodes 5, 6 and 7, the central electrode 5 is connected to an excitation high-voltage power source 8, while the other electrodes 6 and 7 located on the both sides of the central electrode 5 are connected to ground. The structure in which the electrode 5, to which the high voltage is applied, is sandwiched between the grounded electrodes 6 and 7 prevents the plasma produced by the electric discharge from spreading toward the upstream and downstream ends of the gas stream, thereby limiting the substantial plasma generation area to the space between the two plasma generation electrodes 6 and 7.

The excitation high-voltage power source 8 generates a low-frequency high AC voltage. Its frequency is within a range from 50 Hz to 100 kHz, and more preferably from 100 Hz to 20 kHz. The AC voltage may have any waveform, such as sine waves, rectangular waves, triangular waves or sawtooth waves.

A recoil electrode 10, a bias electrode 11 and an ion-collecting electrode 12 are arranged in the lower portion of the cylindrical tube 2 (the downstream side of the gas stream) along the gas-flow direction, with intervening insulators 13 and 14 made of alumina, PTFE resin or other materials. These electrodes each consist of a cylindrical body having the same inner diameter. These cylindrical bodies internally form a gas passage continuously extending from the gas passage 4 in the cylindrical tube 2. These electrodes 10, 11 and 12 are directly exposed to the gas inside the gas passage. A capillary tube 15 is inserted in the gas passage from a gas discharge port disposed at the lower end of the gas passage. Through the capillary tube 15, a predetermined amount of sample gas containing a sample component to be detected is supplied.

The recoil electrode 10 is a grounded electrode for suppressing charged particles in the plasma from reaching the ion-collecting electrode 12 arranged in a downstream side. This is effective for reducing the noise and improving the S/N ratio. The bias electrode 11 is connected to a bias direct-current power source 17 included in an ion-current detection unit 19. The ion-collecting electrode 12 is connected to a current amplifier 18, which is also included in the ion-current detection unit 19.

The discharge ionization current detector 1 according to the present embodiment distinguishingly includes, as an emission timing detection means of the present invention, a current detector 20 disposed between the excitation high-voltage power source 8 and the electrode 5, for detecting the discharge current supplied to the electrode 5. A detection signal produced by the current detector 20 and an output signal from a current amplifier 18 are inputted into an output extraction unit 21 serving as a signal extraction means of the present invention. The output extraction unit 21 is triggered by the detection signal produced by the current detector 20 to extract the output signal from the current amplifier 18 for a predetermined time period, and outputs a voltage signal obtained by integrating the current signal during the time period.

A measurement operation of the discharge ionization current detector 1 is described with reference to FIG. 2 in addition to FIG. 1. In FIG. 2, (*a*) shows a waveform of an output voltage from the excitation high-voltage power source 8; (*b*) shows a waveform of a detection signal produced by the current detector 20; and (*c*) shows a waveform of an output signal from the current amplifier 18. It should be noted that these are actually measured waveforms obtained with a prototype device of the present invention.

As indicated by the downward-pointing arrow in FIG. 1, the predetermined flow rate of helium, which serves as the plasma gas, is supplied into a gas supply port 3. Furthermore, as indicated by the upward-pointing arrow in FIG. 1, sample gas is supplied into the capillary tube 15. The plasma gas is a kind of gas that can be easily ionized, examples of which include helium, argon, nitrogen, neon, xenon and any mixture of two or more of these elements. The helium gas flows downward through the gas passage 4 to join the sample gas supplied through the capillary tube 15, then flows downward through a flow passage outside of the capillary tube 15, and is eventually discharged from a gas discharge port 16 at the lower end of the gas passage.

When the helium gas is passing through the gas passage 4 in the previously described manner, the excitation high-voltage power source 8 is energized under the control by a non-illustrated controller, to apply a low-frequency high AC voltage, which is shown in FIG. 2 (*a*), between the plasma generation electrode 5 and each of the other electrodes 6 and 7. As a result, electric discharge occurs between the plasma generation electrode 5 and each of the electrodes 6 and 7. This electric discharge is dielectric barrier discharge since it is induced through the dielectric coating layer (the cylindrical tube 2). Due to this dielectric barrier discharge, the helium gas flowing through the gas passage 4 is ionized over a broad area. Thus, a cloud of plasma (i.e. atmospheric non-equilibrium micro-plasma) is created.

The low-frequency AC voltage is continuously applied to the electrode 5, while the electric discharge occurs between the electrode 5 and each of the electrodes 6 and 7 in pulses only when the AC voltage is in a specific phase position. In FIG. 2(*b*), the waveform of a discharge current detection signal shows that sharp peaks extending in the positive (upward) and negative (downward) directions are superimposed on a sine wave having the same cycle as the excitation-voltage waveform. The sine wave is measured even when the plasma is not present. Actually, this sine wave is created by a charging current, which has no relation to the electric discharge. On the other hand, the peaks which appear at a point in time when plasma is created are due to the electric discharge. Within each cycle of the excitation voltage waveform, a sharp peak extending in the positive direction appears once every half cycle where a positive voltage is applied to the electrode 5, while a sharp peak extending in the negative direction appears once every half cycle where a negative voltage is applied to the electrode 5. In other words, both the positive voltage discharge and negative voltage discharge respectively occur once every cycle of the excitation voltage.

The plasma created by the previously described electric discharge emits light. The light travels through the gas passage 4 to a region where the sample gas is supplied, and causes the molecules (or atoms) of a sample component in the sample gas to be ionized primarily by the photoionization. The resulting sample ions give electrons to or receive electrons from the ion-collecting electrode 12 by an action of a bias DC voltage at a level of 100V to 200V applied to the bias electrode 11. As previously described, the electric discharge occurs in pulses, and the plasma is also created in pulses. Accordingly, the light of the plasma emission intermittently generates ions originating from the sample component. Furthermore, the lifetime of the generated ions is relatively short, that is, merely a level of 10 to several tens μsec. Therefore, a current of ions reaching the ion-collecting electrode 12 flows only for a short period of time from the time point where the plasma emission occurs. This makes an output of the current amplifier 18 be rendered as shown in FIG. 2(*c*).

Conventionally, the current signal as shown in FIG. 2(*c*) has been integrated for every unit of time to be converted to a voltage signal and outputted. On the other hand, in the device according to the present embodiment, only a current signal obtained during a time period where a current of ions originating from the sample component flows is extracted in the output extraction unit 21 to be converted into a voltage signal. Specific descriptions are: Since, in FIG. 2(*b*), the leading edge of the detection signal obtained by the current detector 20 rises precipitously, the discharge current can be easily discriminated from the charging current. In view of this, the output extraction unit 21 detects the precipitous-rise portion of the discharge current detection signal, and generates a trigger signal. Then, the output extraction unit 21 extracts the current signal inputted from the current amplifier 18 only for a predetermined time period (for example, for a length of time from 10 to several tens μsec) from the generation of the trigger signal (at a timing shown in FIG. 2(*d*)), and converts the current signal into the voltage signal. This makes it possible to extract and measure only the ion current signal originating from the sample component, which flows in the form of pulses synchronized with the plasma emission.

As previously described, the current signal inputted from the current amplifier 18 for a time period except for the period in which the current signal is extracted does not contain any information relating to the ions originating from the sample component, but contains only a noise component. In a conventional device, a measurement has been implemented in such a manner that such a current signal has been averaged for every unit of time. Accordingly, the influence of the noise component is relatively large, so that a favorable S/N ratio is hard to be obtained. In contrast, in the device according to the present embodiment, the current signal obtained only in a time range during which information relating to the ions originating from the sample component is contained is averaged and converted into the voltage signal. Therefore, the influence of the noise component is relatively small and a favorable S/N ratio can be obtained.

In this way, in the discharge ionization current detector 1, the detection signal depending on the amount (concentration) of the sample component contained in the introduced sample gas can be obtained with the high S/N ratio.

The amount of ion generation by the photoionization depends on the brightness of light. As shown in FIG. 2(*b*), the discharge current supplied by the electric discharge with the negative voltage is smaller than that with the positive voltage. This means that the brightness of the light at the plasma emission by the electric discharge with the negative voltage is lower than that with the positive voltage. As a result, as shown in FIG. 2(*c*), the ion current detected at the negative voltage discharge becomes small. In view of this, more preferably, the discharge current detection signal corresponding to the precipitous-rise portion in FIG. 2(*b*) may be detected only in a time period in which the excitation voltage has the positive polarity, so that the trigger signal is generated, thereby extracting only the ion current signal detected at the time of the electric discharge with the positive voltage. This can further improve the S/N ratio of the signal extracted by the output extraction unit 21.

Next, a calculation example of an improvement effect of the S/N ratio in the previously described embodiment is described. FIG. 3 is an enlargement diagram of a peak portion of the ion current detection signal in FIG. 2(*c*) at a time when a positive voltage is applied. The peak shows an output of the current amplifier having a gain of $10^7$ V/A. This means that the peak current of about 300 nA is obtained. Calculating the area of this peak produces a result of 9.0 V·μsec. Even if the area is integrated for a broader range of 10 to 40 μsec time range in FIG. 3 taking jitter into account, the output voltage of 300 mV can be obtained. Meanwhile, if the complete area in a single cycle of 2.5 msec is integrated and calculated without limiting the time range, the obtained output voltage is merely 3.6 mV. Based on this result where the output voltage of 3.6 mV is obtained in the conventional device while the output voltage of 300 mV is obtained in the device of the present embodiment, a simple calculation can be made to confirm that the S/N ratio is increased to about 80 times as high as the level achieved by the conventional device.

Figure 4:
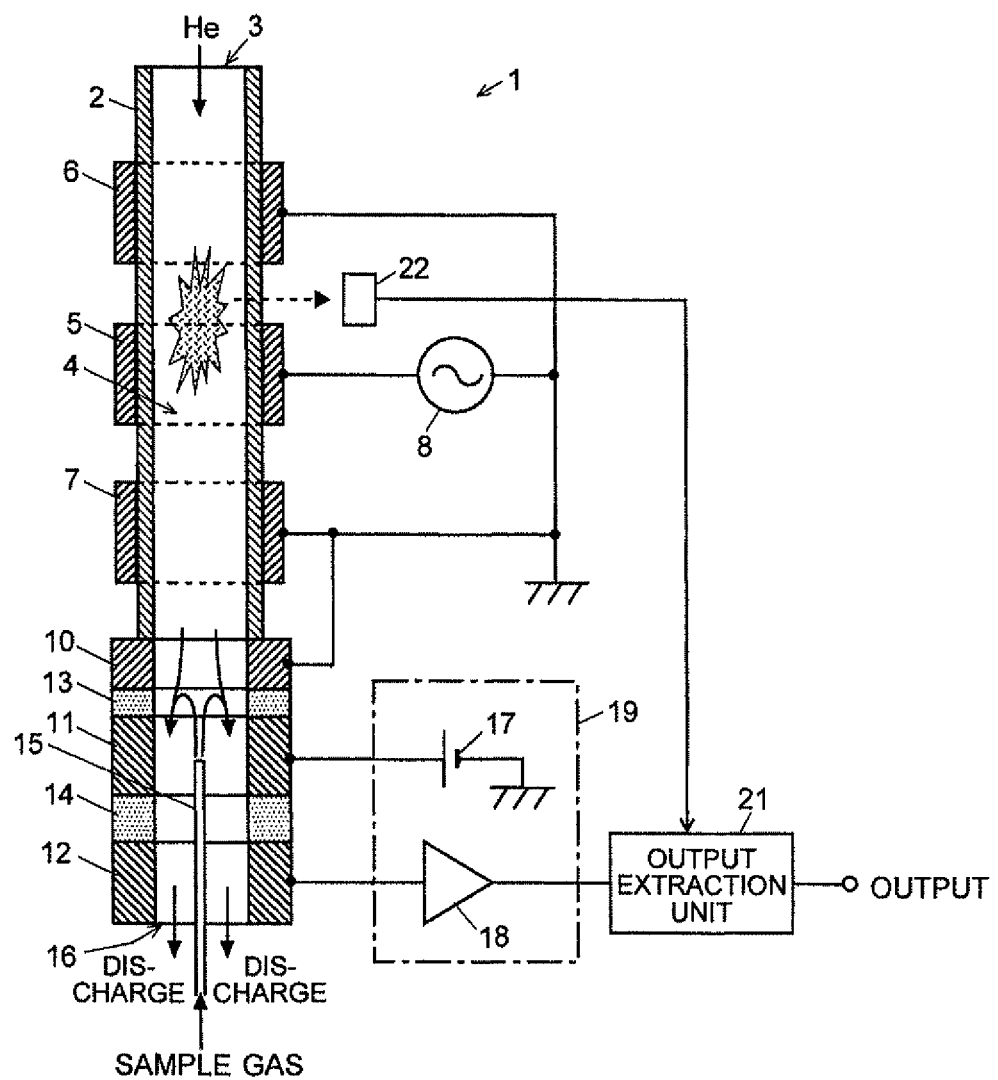
FIG. 4 is a schematic configuration diagram showing a discharge ionization current detector according to another embodiment of the present invention.

FIG. 4 is a schematic configuration diagram showing a discharge ionization current detector according to another embodiment of the present invention. The components identical or corresponding to the components already described in the embodiment shown in FIG. 1 are denoted by the same numerals. A basic difference from the previously described embodiment exists only in a means for obtaining the timing of the plasma emission by electric discharge. In the previously described embodiment, a discharge current supplied from the excitation high-voltage power source 8 to the electrode 5 is detected, and the timing of the plasma emission is indirectly obtained from the detected signal. On the other hand, in the device according to the present embodiment, a photodetector 22 is disposed outside a transparent or semi-transparent cylindrical tube 2 so as to detect light being generated from the plasma and traveling through the wall surface of the cylindrical tube 2. The timing for extracting the ion current signal is determined based on the detection signal of the photodetector 22. Accordingly, only the ion current signal due to the ions originating from the sample component is selectively extracted, and the detection signal having a high S/N ratio can be obtained.

It should be noted that the previously described embodiments are mere examples of the present invention. Any change, modification or addition appropriately made within the spirit of the present invention will naturally fall within the scope of claims of the present patent application.

EXPLANATION OF NUMERALS

1 . . . Discharge Ionization Current Detector
2 . . . Cylindrical Tube
3 . . . Gas Supply Port
4 . . . Gas Passage
5, 6, 7 . . . Plasma Generation Electrode
8 . . . Excitation High-Voltage Power Source
10 . . . Recoil Electrode
11 . . . Bias Electrode
12 . . . Ion-Collecting Electrode
13, 14 . . . Insulator
15 . . . Capillary Tube
16 . . . Gas Discharge port
17 . . . Bias Direct-Current Power Source
18 . . . Current Amplifier
19 . . . Ion-Current Detection Unit
20 . . . Current Detector
21 . . . Output Extraction Unit
22 . . . Photodetector

What is claimed is:
1. A discharge ionization current detector comprising:
a discharge generation means for generating plasma from a predetermined gas by electric discharge, including a pair of electrodes with at least one surface covered with a dielectric material and a voltage application means for applying a low-frequency AC voltage to the electrodes;

a current detection means for detecting an ion current originating from a gas-phase sample component ionized by an action of the generated plasma;

an emission timing detection means for detecting a timing of a plasma emission intermittently generated due to the electric discharge by the discharge generation means; and a signal extraction means for acquiring a signal corresponding to the ion current detected by the current detection means, for a time period from a substantive generation of the plasma emission to a time point which is set after a lapse of a predetermined time period from a termination of the plasma emission, the predetermined time period being determined by taking a lifetime of ions into account, based on the detection result by the emission timing detection means.

2. The discharge ionization current detector according to claim 1, wherein the emission timing detection means is a photodetection means for detecting plasma emission light.

3. A discharge ionization current detector comprising:

a discharge generation means for generating plasma from a predetermined gas by electric discharge, including a pair of electrodes with at least one surface covered with a dielectric material and a voltage application means for applying a low-frequency AC voltage to the electrodes;

a current detection means for detecting an ion current originating from a gas-phase sample component ionized by an action of the generated plasma;

an emission timing detection means for detecting a timing of a plasma emission intermittently generated due to the electric discharge by the discharge generation means; and a signal extraction means for acquiring a signal corresponding to the ion current detected by the current detection means at a timing synchronized with the plasma emission based on the detection result by the emission timing detection means, wherein the emission timing detection means is a current detection means for detecting a current supplied from the voltage application means to the electrodes.

4. The discharge ionization current detector according to claim 3, wherein the emission timing detection means is a photodetection means for detecting plasma emission light.

5. A discharge ionization current detector comprising:

a discharge generation means for generating plasma from a predetermined gas by electric discharge, including a pair of electrodes with at least one surface covered with a dielectric material and a voltage application means for applying a low-frequency AC voltage to the electrodes;

a current detection means for detecting an ion current originating from a gas-phase sample component ionized by an action of the generated plasma;

an emission timing detection means for detecting a timing of a plasma emission intermittently generated due to the electric discharge by the discharge generation means; and a signal extraction means for acquiring a signal corresponding to the ion current detected by the current detection means at a timing synchronized with the plasma emission based on the detection result by the emission timing detection means, wherein the signal extraction means acquires a signal corresponding to the ion current detected by the current detection means at a timing synchronized with the plasma emission during a time period in which a positive voltage is applied to a high-voltage electrode between the pair of electrodes included in the discharge generation means based on the detection result by the emission timing detection means.

6. The discharge ionization current detector according to claim 5, wherein the emission timing detection means is a photodetection means for detecting plasma emission light.

\* \* \* \* \*